United States Patent
Pedrazzini

(10) Patent No.: US 9,792,415 B2
(45) Date of Patent: Oct. 17, 2017

(54) DISTRIBUTED AUTOMATION APPARATUS FOR LABORATORY DIAGNOSTICS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 0 days.

(21) Appl. No.: 14/403,466

(22) PCT Filed: May 23, 2013

(86) PCT No.: PCT/EP2013/060584
§ 371 (c)(1),
(2) Date: Nov. 24, 2014

(87) PCT Pub. No.: WO2013/174906
PCT Pub. Date: Nov. 28, 2013

(65) Prior Publication Data
US 2015/0169846 A1 Jun. 18, 2015

(30) Foreign Application Priority Data
May 24, 2012 (IT) .............................. MI2012A0902

(51) Int. Cl.
G06F 19/00 (2011.01)
G06Q 50/22 (2012.01)
G06F 19/22 (2011.01)
G01N 35/00 (2006.01)
G05B 15/02 (2006.01)

(52) U.S. Cl.
CPC ..... *G06F 19/366* (2013.01); *G01N 35/00871* (2013.01); *G05B 15/02* (2013.01)

(58) Field of Classification Search
CPC .. G06F 19/363; G06F 19/3475; G06F 19/366; G06F 19/14; G06F 19/22; G06F 19/3418; G06F 19/3493; G06Q 50/24; G06Q 50/18; G06Q 50/22; G06Q 10/10; G06Q 10/06; G06Q 10/083; G06Q 10/087; G06K 17/0022; G06K 2017/0045; G07F 11/002
See application file for complete search history.

(56) References Cited

U.S. PATENT DOCUMENTS

| | | | |
|---|---|---|---|
| 5,988,857 A | 11/1999 | Ozawa et al. | |
| 2005/0036912 A1 | 2/2005 | Yamakawa et al. | |
| 2006/0148063 A1 | 7/2006 | Fauzzi et al. | |
| 2007/0254277 A1* | 11/2007 | Scrabeck ......... | G01N 35/00722 435/4 |
| 2012/0109531 A1 | 5/2012 | Knafel et al. | |

* cited by examiner

*Primary Examiner* — Maroun Kanaan
(74) *Attorney, Agent, or Firm* — Jacobson Holman, PLLC.

(57) ABSTRACT

A distributed automation apparatus for laboratory diagnostics is described, comprising modules for processing biological products transported on an automatic conveyor and modules for interfacing with analysis devices, both said modules being connected to said automatic conveyor, each of said modules is independent of the other modules, it being provided with its own control board, which allows it to work autonomously and independently of a central control unit which provides a worklist to each node which is dynamically read and updated by said control unit, and said module reading and updating said, worklist.

4 Claims, 2 Drawing Sheets

DISTRIBUTED AUTOMATION APPARATUS FOR LABORATORY DIAGNOSTICS

FIELD OF THE INVENTION

The present invention relates to a distributed automation apparatus for laboratory diagnostics.

DESCRIPTION OF RELATED ART

Nowadays, in laboratories for testing biological material specimens it is typical to use motor-driven systems along which the specimens travel, inside dedicated containers of biological products, encountering various devices or modules along their path, adapted to carry out various treatments (uncapping, recapping of the containers themselves, centrifugation of their content and so on) on the specimens themselves, or other modules having a different function, i.e. interfacing the containers of biological products with the actual testing devices of the specimen itself.

The automated management of the addressing of the specimens present along the various modules is controlled by a central control unit, i.e. a computer provided with software designed to suitably sort the specimens according to the specific operating requirements of each one of them; such software actually contains all the information needed for the operations required by every single specimen in its path along the whole automation.

In this respect, the system architecture is a centralized architecture since the task of supervising the whole flow of operations as well as the step-by-step management of the various actuation steps of every single module are a prerogative only of such a central control unit. Each of the modules present along the automation (either for pre-testing, post-testing or modules for interfacing with analyzers) is a simple executor of instructions received from the central control unit, and must therefore be guided by the latter in carrying out every single operating step.

Problems occur in a centralized architecture of this type since the central control unit is designed to manage the components (both hardware and software) which characterize every operating instance of a specific module.

The introduction of multiple instances of a same module along an automation system involves significant design modifications to the central control unit, which must be configured on the basis of the concurrent presence of multiple identical modules capable of carrying out the same operations.

Therefore, since according to the specific requirements of each laboratory each system has different modules as well as a different number of instances for each module, the design modifications related to the central control unit are specific for each one of the above systems, i.e. they are not reproducible or reusable from one to the other.

Moreover, in case of failure or start of a maintenance procedure on even one of the modules present along the automated system, the whole system must be set to stand-by since the centralized management by the control unit recognizes the faulty module as system "bottleneck" and since the operations related to it are strictly related to those of the other modules (i.e. it is not independent of the other ones from the software point of view), the system is not capable of temporarily isolating only the faulty module, continuing with the specimen processing by the other modules.

Eventually, an operator's management of the manual controls to be imparted to the various automation components is possible thanks to the presence of a single Graphical User Interface (GUI) residing on site close to the automation; this requires the physical presence of an operator close to the system at any time for carrying out the control operations and optionally the addressing of specimens and the dynamic reassignment of tasks to the various system component modules.

BRIEF SUMMARY OF THE INVENTION

The object of the present invention is to provide an automation apparatus which, from the architectural point of view, allows the above-described problems to be overcome while ensuring a dynamic management of the addressing of biological material specimens along the apparatus itself, and so that the specimens flow in a smoother manner compared to the known solutions.

A further object consists in preventing the whole automation apparatus from stopping in case of failure or maintenance of one or more of the modules involved in the automation.

Last but not least, an object is to get free of the need of having an operator always present close to the automation system.

These and other objects are achieved by a distributed automation system for laboratory diagnostics comprising modules for carrying out operations of various types on biological product containers and modules for interfacing with devices for testing biological product specimens, both said types of modules being connected to an automatic conveyor designed to transport said containers from one module to the other, characterized in that each of said modules is autonomous in the management of its local process, irrespective of the specificity of the operations carried out by said module, it being guided in the performance of said operations by a control board thereof connected to a central control unit.

BRIEF DESCRIPTION OF THE DRAWINGS

These and other features of the present invention will appear more clearly from the following detailed description of an embodiment thereof, made by way of a non-limiting example with reference to the accompanying drawings, in which.

DETAILED DESCRIPTION OF THE INVENTION

A laboratory automation apparatus consists of an automatic conveyor designed to transport, by means of suitable conveyor belts, biological product containers, for example tubes inserted in dedicated transport devices, from one point to the other of the apparatus itself and in particular, from one to the other of modules present in the apparatus. More precisely, they are modules 1 capable of autonomously managing operations for processing the biological product containers carrying out the most varied operations typical of laboratory systems of this type (and thus, for example, uncapping, recapping of tubes, centrifugation of their content, separation of the content of the parent tube into multiple daughter tubes and so on), or modules 2 which carry out no operations on tubes but are interfacing modules of the automation apparatus with the actual analysis devices 20 for testing biological product specimens of tubes.

Naturally, each of modules 1, 2 is only involved with a certain number of tubes according to the different treatments or tests that each specimen requires; therefore, tubes inserted in dedicated transport devices (also called "carriers", not shown in the figures) travel along the automatic conveyor and are addressed to the suitable modules 1,2.

Figure 1:
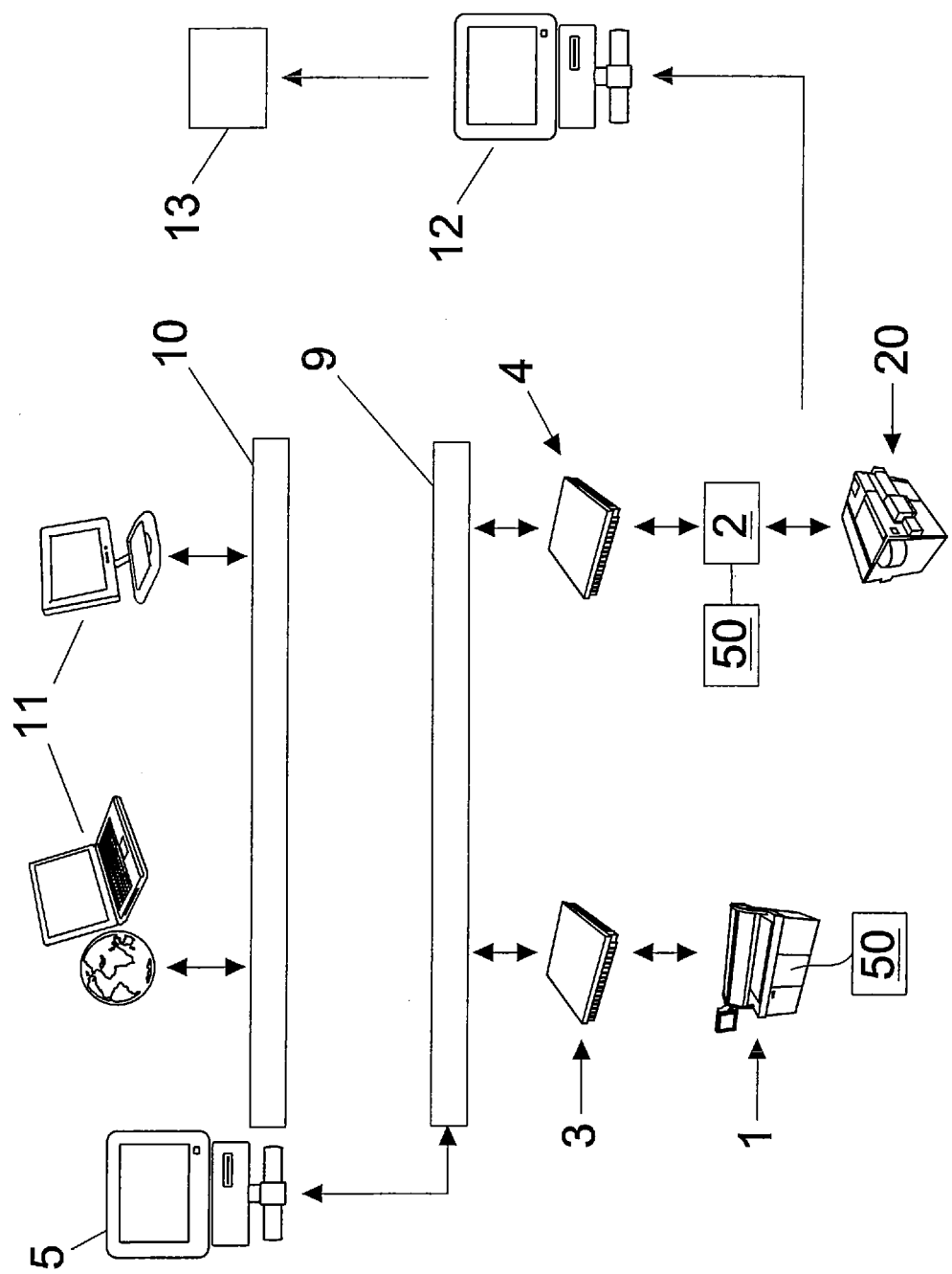
FIG. 1 shows a block diagram with the main elements of an apparatus according to the invention.

Each module 1, 2 present along the automation apparatus corresponds to a node 3, 4 (FIG. 1, with reference to modules 1, 2, respectively) which at a software level has the task of sorting or not each of the transport devices arriving at module 1, 2 itself, and thus, for example, the operations of diverting specimens contained in tubes from a main lane to a secondary lane of conveyor or of addressing the specimens contained in tubes towards U- or T-shaped portions of conveyor to make them interface with module 1, 2.

The whole operation flow is managed by a central control unit 5 which interfaces with each node 3, 4 present in the apparatus by providing a worklist 6 to node 3, 4 itself, which worklist contains a list of the transport devices to be processed by module 1, 2, a series of variables representing various attributes and/or identification codes referred to each transport device and/or related tube in the automation apparatus, the status of the transport device and the status of tubes. Said central control unit 5 dynamically reads and updates said worklist 6.

Worklist 6 provides to every node 3, 4 precise information about the status of each of the transport devices (and of the possible related tube contained in each of them) at any time. Each module 1, 2 interfaces with the transport devices and with tubes and as a result, according to the most suitable sequence of operations that each module 1, 2 determines independently from the central unit 5, each module 1, 2 can carry out the processing of the transport devices themselves and of tubes themselves one by one, dynamically reading and updating worklist 6.

Naturally, the own intelligence of the whole apparatus, managed by the central control unit 5 addresses the transport devices and the related tubes by updating worklist 6, which is read by nodes 3, 4 which sort the biological product containers, only towards the suitable modules 1 which carry out the operations needed by each tube and/or towards the interfacing modules 2 with the suitable analysis devices 20 of the specimen contained in tubes, Nodes 3, 4 communicate the sorting to the central control unit 5 so that the central control unit 5 updates worklists 6 at nodes 3,4.

However, more in general, the addressing may also relate to empty transport devices, i.e. not containing tubes, because for example it may be necessary for the central control unit 5 to update worklists 6 to make the transport devices be sorted at nodes 3, 4 by diverting them from a main lane to a secondary lane of conveyor irrespective of whether such transport devices contain or not a tube.

The central control unit 5 is a computer provided with software 7 which is capable of communicating with the single nodes 3, 4 of the automation apparatus and of dynamically reading and updating worklists 6 related to each node 3, 4 according to the changing processing requirements of tubes, which requirements may change anytime in the automation apparatus. Said updates may relate for example to the addition or deleting of transport devices (and of the related specimens contained in tubes) to/from a worklist 6, or the modification of the processing priority level of a specimen contained in tube, and so on.

Likewise, the information and the updates about the current status of each transport device traveling along the automation apparatus must be updated in worklists 6 to be read by the central control unit 5.

Figure 2:
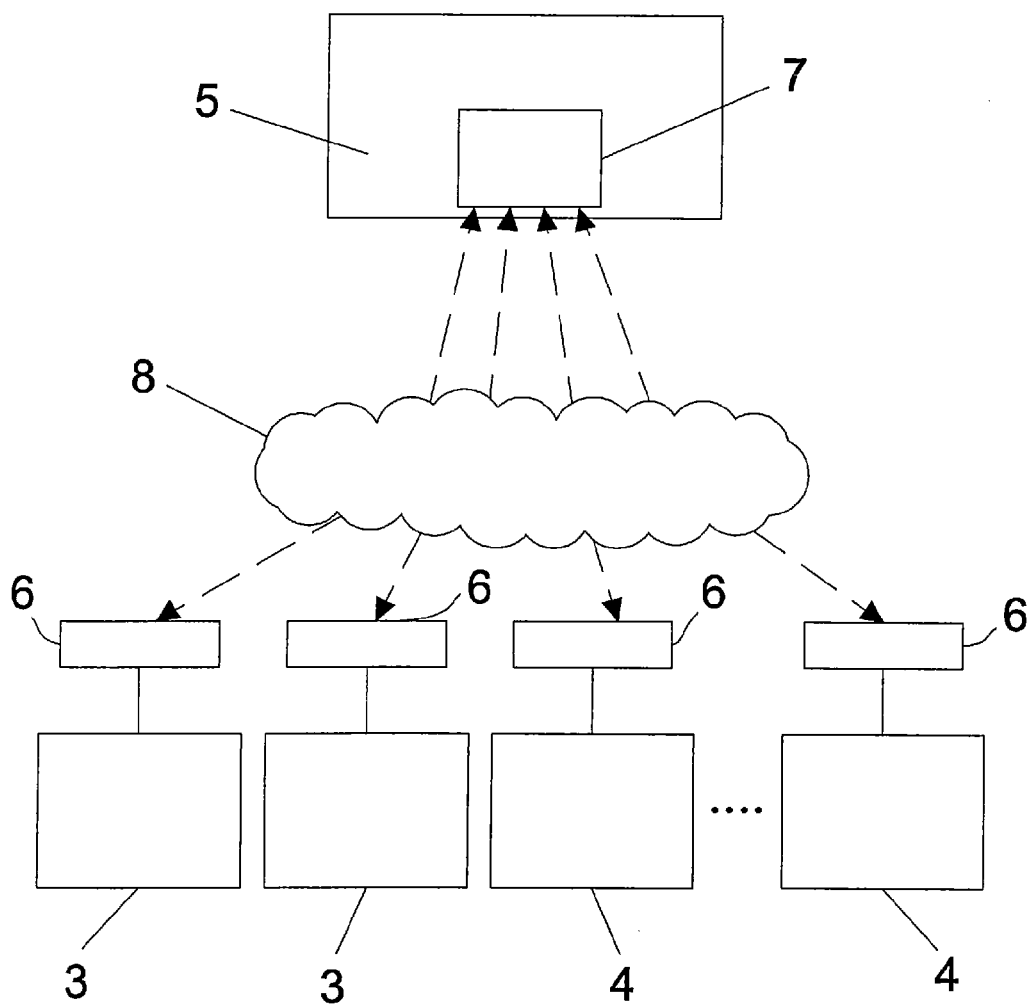
FIG. 2 show in more detail the interfacing between the central control unit and the various modules.

In the practice, the communication between the control unit 5 and the various nodes 3, 4 is two-directional; the interfacing takes place by means of a CAN network 8, and the protocol used is CANopen (FIG. 2).

The central control unit 5 is therefore connected on one side to nodes 3, 4 by means of an Automation Network 9 (FIG. 1), while on the other side it is connected via Ethernet 10 to the various Graphical User Interfaces (GUI) 11 designed for an operator's management of the controls to be manually imparted (by means of a practical touch-screen) to each of modules 1, 2, or even for activities of log analysis or diagnostics of the single modules. The central control unit 5 updates the suitable worklist 6 at the suitable mode 3, 4 so that the operator's manual control adequately reaches the suitable module 1, 2. Such a connection may either be direct by means of a LAN cable, or remote through the Internet. Nodes 3, 4 are in turn two-directionally connected by the respective automation modules 1 or by the interfacing modules 2 to analysis devices 20. Modules 1, 2 update the respective worklists 6 as they carry out the operations independently of the central control unit 5.

Moreover, the results of the various tests on specimens carried out by analysis devices 20 of the automation apparatus and which can be displayed on the screen of each of said GUIs 11, are then provided to the Laboratory Information System (LIS) 12, i.e. the system that manages the patients' personal information and, through the processing and storage of the information generated by the various machines present along the automation apparatus, it is capable of assembling all these data and output data interpretable for a medical report. In turn, LIS 12 can interface in a broader sense with the whole Hospital Information System (HIS) 13, intended as the set of all the information instruments used in the healthcare field for managing both administration and clinical flows of a hospital.

Considering the automation apparatus as a whole, obtaining a desired treatment throughput of a certain number of specimens in the predetermined unit of time is determined by the joint action of the plurality of modules 1, 2 belonging to the whole automation apparatus. Therefore, it is suitable to maximize both the throughput of the single module 1, 2 and, in a broader sense, synchronize the joint action of all modules 1, 2 present for maximizing the overall throughput of the automation apparatus.

The innovative feature of the invention is determined by the fact that each of modules 1, 2 used in the automation apparatus is independent of the others, being provided with its own control board 50 which allows it to autonomously manage the flow of operations for processing the biological material specimens contained in tubes and the operations to be carried out on the same on the basis of the reading of worklist 6 and updating it as module 1, 2 carries out the processing operations. The interfacing with the central control unit 5 takes places when the control unit 5 communicates with the node 3, 4 concerned by reading, communicating to it or updating worklist 6, and subsequently, on the other hand, in the step in which module 1, 2 reads and updates worklist 6, it is node 3, 4 that communicates with the control unit 5. Module 1, 2 communicates the results of its processing on the specimens to node 3, 4 and node 3, 4 in turn communicates said results to the control unit 5. In addition, in order to maintain the traceability related to the evolution of the transport device, and optionally of the related tube, into module 1, 2 during its processing, continuous updates are provided by module 1, 2 to node 3, 4 and hence to the central control unit 5 about the logical/physical status of each transport device and of tubes.

During the processing of specimens, each module 1, 2 manages the operations autonomously and independently of the central control unit 5; in fact, once module 1, 2 takes charge of the transport device, the process logic is a prerogative of module 1, 2 itself, unlike what happens for the modules of the known systems in which the logic is a property of the central control unit 5. In this respect, therefore, a switch has been advantageously made from a centralized architecture to a faster, distributed one.

In other words, the source code related to the management of each module 1, 2 connected to the apparatus is now directly contained in module 1, 2 itself, or better in its control board 50, while in known apparatus the code related to the management of each single module is an integral part of the single code residing in the central control unit 5.

In this way now, once it has received (through the CAN network 8 and the related communication protocol CANopen) its worklist 6 from the respective node 3, 4, each module 1, 2 is then capable of autonomously managing the relevant flow of operations and thus its capability of processing the specimens contained in tubes; on the contrary, this does not happen in the known solutions where each module still needs to be instructed step by step by the central control unit 5 in carrying out each operation, even minimal ones.

This implies a further important aspect related to a distributed architecture like that of the invention: in fact, if for any reason it is necessary to modify a part of the source code referred to one of modules 1, 2 of the apparatus, such modification as said concerns a source code which is unrelated and independent of that of the other modules 1, 2 and of the central control unit 5; on the contrary, in known solutions, whatever is the module to be acted upon, the overall code to be modified is always that residing in the central control unit 5, with noticeable complications in writing the modification to the code itself, since it is always necessary to keep into account the interrelations existing between the module concerned and all the others, also the possible ones not concerned by any modification.

This leads to a further noticeable practical advantage: according to the present invention, if maintenance or troubleshooting operations need to be carried out on one of modules 1, 2 belonging to the automation apparatus, it may be set to stand-by and temporarily isolated from the rest of the automation apparatus, which continues to operate normally. On the contrary, this is not possible in known solutions because since they are characterized by a centralized architecture, as said, it is as if modules 1, 2 were all always connected to each other, and thus setting one to stand-by equals to setting the whole automation apparatus to stand-by.

Moreover, with a distributed architecture it is possible to interface the automation apparatus with a theoretically unlimited plurality of modules 1, 2, even optionally different units of modules 1, 2 adapted to carry out the same function, for example in different points along the automation apparatus for further increasing the processing speed of the biological specimens. In this way, the above-described problem referred to the known solution is overcome, i.e. the difficulty of interfacing multiple instances of the same module with a single system, due to the design modifications that this implies at the level of the central control unit 5. In the above solution, on the other hand, any addition of new modules 1, 2 does not imply such modifications and they can therefore be freely added according to the requirements of each system.

Moreover, the apparatus according to the present invention is configurable to be managed through Ethernet 10, via a direct connection with LAN cable or remotely, by connecting to the Internet, from a plurality of Graphical User Interfaces 11. They may be present in a variable number and noticeably positioned in different points of the laboratory or even outside the same. This is also an absolutely innovative feature compared to the known automation apparatus which can only be managed by a single Graphical User Interface present on site where the automation is located.

In the practice, it has been seen that the distributed automation apparatus as described can achieve the intended objects ensuring the independence, within the apparatus, of each of the modules belonging to the automation as well as the possibility of inserting a theoretically unlimited number of modules in the apparatus itself, either modules 1 designed to carry out operations on tubes containing the specimens or modules 2 for interfacing with analysis devices 20 of the biological material specimens contained in tubes themselves.

In case of failure or maintenance on one of modules 1, 2, the distributed logic architecture allows the rest of the automation apparatus to still be kept operating by temporarily isolating only module 1, 2 concerned by the failure and ensuring the normal operation of the other modules 1, 2 present.

Moreover, the possibility of imparting controls to each of modules 1, 2 present in the automation apparatus from a certain number of different workstations 11 allows the addressing of the specimens contained in tubes in the automation apparatus to be modified according to any type of new requirement that may arise, without the presence of an operator being strictly required in the testing laboratory but rather, optionally remotely through an Internet connection, and thus even at thousands kilometers distance and at any time of the day, for example at night-time.

Moreover, since the control unit does not need to instruct each module 1, 2 step by step anymore in the performance of every single operation, the information flow to be exchanged between the central control unit 5 and the various modules 1, 2 is reduced compared to the known solutions, since modules 1, 2 are now managed by an autonomous control board 50 and are therefore independent of the central control unit 5.

Several changes and variations may be made to the invention thus conceived, all falling within the scope of the inventive concept.

In the practice, the materials used as well as shapes and sizes, may be any, according to the requirements.

The invention claimed is:

1. A distributed automation apparatus for laboratory diagnostics comprising
    first modules for carrying out operations of various types on biological product containers inserted in dedicated transport devices which are transported on an automatic conveyor and second modules for interfacing with analysis devices of biological product specimens, both the first and second modules being connected to said automatic conveyor,
    a central control unit comprising a first computer processor in communication with a first storage device storing instructions that are executable to enable the first computer processor to provide worklists to respective first and second modules dynamically read and updated by said central control unit and to temporarily isolate faulty or inoperable first or second modules from the rest of the automation apparatus, which continues to operate normally, each of said first and second modules being independent with respect to the other first and second modules, and being provided with its own control board comprising a second computer processor in communication with a second storage device storing instructions that are executable to enable the second computer processor to autonomously manage the flow of operations for processing the biological material specimens, said apparatus also comprises nodes between said central control unit and said first or second modules, one node for each first or second module, said central control unit being connected to the nodes by an Automation Network, said central control unit transmitting a worklist to each node for each module, wherein each module reads and updates the respective worklist at the respective node by the results of its processing on the specimen, each node in turn communicating said results to the central control unit.

2. The apparatus according to claim 1, wherein the connection between said first and second modules, said nodes and said central control unit is realized through a CAN network and a related communication protocol of CANopen type.

3. The apparatus according to claim 1, wherein the central control unit is connected via Ethernet to a plurality of Graphical User Interfaces designed for an operator's management of the controls to be manually imparted to each of the first and second modules or even for activities of log analysis or diagnostics of the single first or second modules.

4. The apparatus according to claim 1, wherein the results of the various tests on the specimens carried out by the analysis devices are provided to a Laboratory Information System comprising a computer processor suitable for interfacing with a whole Hospital Information System, intended as the set of ail the information instruments used in healthcare field for managing both administration and clinical flows of a hospital.

* * * * *